United States Patent [19]

Maloy et al.

[11] Patent Number: 5,470,950
[45] Date of Patent: Nov. 28, 1995

[54] BIOLOGICALLY ACTIVE AMPHIPHILIC PEPTIDE COMPOSITIONS AND USES THEREFOR

[75] Inventors: W. Lee Maloy; U. Prasad Kari, both of Lansdale, Pa.; Jon I. Williams, Robbinsville, N.J.

[73] Assignee: Magainin Pharmaceuticals Inc., Plymouth Meeting, Pa.

[21] Appl. No.: 193,521

[22] Filed: Feb. 8, 1994

Related U.S. Application Data

[63] Continuation of Ser. No. 870,960, Apr. 20, 1992, abandoned, which is a continuation-in-part of Ser. No. 760,054, Sep. 13, 1991, abandoned.

[51] Int. Cl.$^6$ ................................................ A61K 38/03
[52] U.S. Cl. ..................... 530/324; 530/325; 530/326; 530/327; 530/328; 530/329
[58] Field of Search ................................ 514/12; 530/324, 530/325–329

[56] References Cited

U.S. PATENT DOCUMENTS 5,294,605  3/1994  Houghten et al. ................ 514/13

FOREIGN PATENT DOCUMENTS 04371  5/1989  WIPO .

OTHER PUBLICATIONS

Mihara, et al., Peptide Chemistry (1985), pp. 223–228.
Lee, et al., Peptide Chemistry (1985), pp. 317–320.

*Primary Examiner*—Jill Warden
*Assistant Examiner*—Benet Prickril
*Attorney, Agent, or Firm*—Finnegan, Henderson, Farabow, Garrett & Dunner

[57] ABSTRACT

Biologically active amphiphilic peptides including one of the following basic structures: I. $R_1-R_2-R_2-R_1-R_2-R_2-R_1-R_1-R_2-R_1-R_1$; II. $R_2-R_1-R_2-R_2-R_1-R_1-R_2-R_2-R_1-R_2-R_2$; III. $R_1-R_2-R_2-R_1-R_1-R_2-R_2-R_1-R_2-R_2-R_1-R_1-R_2-R_3$; IV. $R_1-R_2-R_1-R_1-R_2-R_2-R_1-R_1-R_2-R_2-R_4$; V. $R_1-R_1-R_2-R_2-R_1-R_2-R_2-R_1-R_1-R_2-R_2-R_3$; or VI. $R_1-R_1-R_3-R_2-R_1-R_1-R_1-R_1-R_1-R_1-R_2-R_1-R_1-R_2-R_2-R_1-R_1-R_1-R_1-R_1-R_2-R_2-R_1$.

$R_1$ is a hydrophobic amino acid and $R_2$ is a basic hydrophilic or neutral hydrophilic amino acid, $R_3$ is a neutral hydrophilic amino acid, and $R_4$ is a neutral hydrophilic amino acid or proline.

There is also provided a biologically active amphiphilic peptide having a structural formula selected from the group consisting of:

(a) $R_1-R_2-R_2-R_1-R_2-R_2-R_1$;
(b) $R_1-R_1-R_2-R_2-R_1-R_2-R_2-R_1$;
(c) $R_2-R_1-R_1-R_2-R_2-R_1-R_2-R_2-R_1$;
(d) $R_2-R_2-R_1-R_1-R_2-R_2-R_1-R_2-R_2-R_1$; and
(e) $R_1-R_2-R_2-R_1-R_1-R_2-R_2-R_1-R_2-R_2-R_1$; wherein $R_1$ and $R_2$ are are hereinabove described.

Such peptides may be employed as pharmaceuticals.

8 Claims, No Drawings

BIOLOGICALLY ACTIVE AMPHIPHILIC PEPTIDE COMPOSITIONS AND USES THEREFOR

This application is a continuation of application Ser. No. 07/870,960, filed Apr. 20, 1992, now abandoned, which is a continuation-in-part of application Ser. No. 07/760,054, filed Sep. 13, 1991, now abandoned.

This invention relates to biologically active amphiphilic peptides. More particularly, this invention relates to biologically active amphiphilic peptides useful in pharmaceutical compositions.

In accordance with an aspect of the present invention, there is provided a biologically active amphiphilic peptide which includes the following basic structure $X_{10}$:

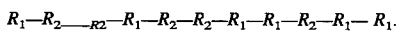

$R_1$ is a hydrophobic amino acid, and $R_2$ is a basic hydrophilic or neutral hydrophilic amino acid.

In one embodiment, the peptide includes the basic structure $Y_{10}$–$X_{10}$ wherein $X_{10}$ is as hereinabove described and $Y_{10}$ is:

(i) $R_1$;

(ii) $R_2$—$R_1$; or (iii) $R_2$—$R_2$—$R_1$, wherein $R_1$ and $R_2$ are is hereinabove described.

The hydrophobic amino may be selected from the class consisting of Ala, Cys, Phe, Gly, Ile, Leu, Met, Pro, Val, Trp and Tyr.

The basic hydrophilic amino acid acids may be selected from the class consisting Lys, Arg, His, Orn, homoarginine (Har), 2, 4-diaminobutyric acid (Dbu), and p-aminophenylalanine. The neutral hydrophilic amino acids may be selected from the class consisting of Asn, Gln, Ser, Thr, and homoserine (Hse). In one embodiment, $R_1$ is leucine. In another embodiment, $R_2$ is lysine. Representative examples of peptides in accordance with this aspect of the present invention include those having the following structures:

(SEQ ID NO: 1)
(SEQ ID NO: 2)
(SEQ ID NO: 3)
(SEQ ID NO: 4)

In accordance with another aspect of the present invention, there is provided a biologically active amphiphilic peptide which includes the following basic structure $X_{12}$:
$R_2$—$R_1$—$R_2$—$R_2$—$R_1$—$R_1$—$R_2$—$R_2$—$R_1$—$R_2$— $R_2$,
wherein $R_1$ is a hydrophobic amino acid and $R_2$ is a basic hydrophilic or neutral hydrophilic amino acid.

In one embodiment $R_1$ is leucine. In another embodiment, $R_2$ is lysine.

In one embodiment, the peptide includes the basic structure $Y_{12}$–$X_{12}$, wherein $X_{12}$ is as hereinabove described, and $Y_{12}$ is:

(i) $R_2$;

(ii) $R_1$—$R_2$;

(iii) $R_1$—$R_1$—$R_2$;

(iv) $R_2$—$R_1$—$R_1$—$R_2$; or (v) $R_2$—$R_2$—$R_1$—$R_1$—$R_2$.

In one embodiment, the peptide may have the following structure;

Lys Lys Leu Leu Lys Lys Leu Lys Lys Leu (SEQ ID NO.:5)
5                              10
Leu Lys Lys Leu Arg Arg
15

In another embodiment, the peptide includes the basic structure $X_{12}$–$Z_{12}$, wherein $X_{12}$ is as hereinabove described, and $Z_{12}$ is:

(i) $R_1$;

(ii) $R_1$—$R_1$;

(iii) $R_1$—$R_1$—$R_2$;

(iv) $R_1$—$R_1$—$R_2$—$R_2$; or $R_1$—$R_1$—$R_2$—$R_2$—$R_1$;

In one embodiment, the peptide may have the following structure:

Lys Leu Lys Lys Leu Leu Lys Lys Leu Lys Lys Leu Leu Lys Lys Leu (SEQ ID NO:6)
5                    10                  15

In another embodiment, the peptide may include the structure:
$(Y_{12})_a$—$X_{12}$—$(Z_{12})_b$, wherein $X_{12}$, $Y_{12}$ and $Z_{12}$ are as hereinabove described, and a is 0 or 1, and b is 0 or 1.

In accordance with another aspect of the present invention, there is provided a biologically active amphiphilic peptide which includes the following basic structure $X_{14}$:
$R_1$—$R_2$—$R_2$—$R_1$  —$R_1$—$R_2$—$R_2$—$R_1$—$R_2$—$R_2$—$R_1$—$R_1$—$R_2$—$R_2$ —$R_3$,
wherein $R_1$ and $R_2$ are as hereinabove described, and $R_3$ is a neutral hydrophilic amino acid.

In one embodiment, the peptide may have the following structure:

(SEQ ID NO: 7 )

In another embodiment, the peptide may have the following structure:

(SEQ ID NO:8)

In accordance with yet another aspect of the present invention, there is provided a biologically active amphiphilic peptide which includes the following basic structure $X_{16}$: $R_1$—$R_2$—$R_1$—$R_1$—$R_2$  —$R_2$—$R_1$—$R_1$—$R_2$—$R_2$—$R_4$, wherein $R_1$ and $R_2$ are as hereinabove described, and $R_4$ is a neutral hydrophilic amino acid or proline.

In one embodiment, the peptide may include the following structure $Y_{16}$–$X_{16}$, wherein $X_{16}$ is the basic peptide structure hereinabove described, and $Y_{16}$ is:

(i) —$R_1$;

(ii) —$R_1$—$R_1$;

(iii) —$R_2$—$R_1$—$R_1$;

(iv) —$R_1$—$R_2$—$R_1$—$R_1$;

(v) —$R_1$—$R_1$—$R_2$—$R_1$—$R_1$;

(vi) —$R_2$—$R_1$—$R_1$—$R_2$—$R_1$—$R_1$; or (vii) —$R_2$—$R_2$—$R_1$—$R_1$—$R_2$—$R_1$—$R_1$, wherein $R_1$ and $R_2$ are as hereinabove described.

In one embodiment, the peptide may include the structure: $X_{16}$–$Z_{16}$, wherein $X_{16}$ is as hereinabove described, and $Z_{16}$ is:

(i) —$R_2$;
(ii) —$R_2$—$R_2$;
(iii) —$R_2$—$R_2$—$R_1$;
(iv) —$R_2$—$R_2$—$R_1$—$R_1$;
(v) —$R_2$—$R_2$—$R_1$—$R_1$—$R_2$;
(vi) —$R_2$—$R_2$—$R_1$—$R_1$—$R_2$—$R_2$; or
(vii) —$R_2$—$R_2$—$R_1$—$R_1$—$R_2$—$R_2$—$R_1$.

In a preferred embodiment, the peptide may have one of the following structures:

(SEQ ID NO:9); or (SEQ ID NO:10).

In another embodiment, the peptide may have the structure $(Y_{16})_a$—$X_{16}$—$(Z_{16})_b$, wherein $X_{16}$, $Y_{16}$, and $Z_{16}$ are as hereinabove described, a is 0 or 1, and b is 0 or 1.

In accordance with another aspect of the present invention, there is provided a biologically active amphiphilic peptide which includes the following basic structure $X_{18}$:
$R_1$—$R_1$—$R_2$—$R_2$—$R_1$—$R_2$—$R_2$—$R_1$—$R_1$—$R_2$—$R_2$—$R_1$—$R_3$,
wherein $R_1$, $R_2$, and $R_3$ are as hereinabove described.

In accordance with another embodiment, the peptide may include the structure $Y_{18}$–$X_{18}$, wherein $X_{18}$ is as hereinabove described, and $Y_{18}$ is:

(i) —$R_1$;
(ii) —$R_2$—$R_1$;
(iii) —$R_2$—$R_2$—$R_1$;
(iv) —$R_1$—$R_2$—$R_2$—$R_1$;
(v) —$R_1$—$R_1$—$R_2$—$R_2$—$R_1$;
(vi) —$R_2$—$R_1$—$R_1$—$R_2$—$R_2$—$R_1$; or
(vii) —$R_2$—$R_2$—$R_1$—$R_1$—$R_2$—$R_2$— $R_1$, wherein $R_1$ and $R_2$ are as hereinabove described.

In another embodiment, the peptide includes the structure $X_{18}$–$Z_{18}$, wherein $X_{18}$ is as hereinabove described, and $Z_{18}$ is:

(i) —$R_1$;
(ii) —$R_1$—$R_5$;
(iii) —$R_1$—$R_5$—$R_5$;
(iv) —$R_1$—$R_5$—$R_5$—$R_3$;
(v) —$R_1$—$R_5$—$R_5$—$R_3$—$R_1$;
(vi) —$R_1$—$R_5$—$R_5$—$R_3$—$R_1$—$R_3$;
(vii) —$R_1$—$R_5$—$R_5$—$R_3$—$R_1$—$R_3$—$R_3$;
(viii) —$R_1$—$R_5$—$R_5$—$R_3$—$R_1$—$R_3$—$R_3$—$R_5$; or
(ix) —$R_1$—$R_5$— $R_5$—$R_3$—$R_1$—$R_3$—$R_3$—$R_5$—$R_3$,
wherein $R_1$ and $R_3$ are as hereinabove described, and $R_5$ is proline.

In one embodiment, the peptide has the following structure:

(SEQ ID NO:11).

In one embodiment, the peptide may have the structure $(Y_{18})_a$—$X_{18}$—$(Z_{18})_b$, wherein $X_{18}$, $Y_{18}$, and $Z_{18}$ are as hereinabove described, a is 0 or 1, and b is 0 or 1.

In accordance with another aspect of the present invention, there is provided a biologically active amphiphilic peptide which includes the following basic structure $X_{20}$:
$R_1$—$R_1$—$R_3$—$R_2$—$R_1$—$R_1$—$R_1$— $R_1$—$R_1$—$R_1$—$R_2$—$R_1$—$R_1$—$R_2$—$R_2$— $R_1$—$R_1$—$R_2$—$R_2$—$R_1$—, wherein $R_1$, $R_2$, and $R_3$ are as hereinabove described. In one embodiment, the peptide may have the following structure:

(SEQ ID NO:12).

In another embodiment, the peptide may include the structure $X_{20}$–$Z_{20}$, wherein $X_{20}$ is as hereinabove described, and $Z_{20}$ is:

(i) —$R_2$;
(ii) —$R_2$—$R_2$;
(iii) —$R_2$—$R_2$—$R_1$;
(iv) —$R_2$—$R_2$—$R_1$—$R_1$;
(v) —$R_2$—$R_2$—$R_1$—$R_1$—$R_2$;
(vi) —$R_2$—$R_2$—$R_1$—$R_1$—$R_2$—$R_2$; or
(vii) —$R_2$—$R_2$—$R_1$—$R_1$—$R_2$—$R_2$—$R_1$.

In accordance with yet another aspect of the present invention, there is provided a biologically active amphiphilic peptide having a structure selected from the group consisting of:

(a) $R_1$—$R_2$—$R_2$—$R_1$—$R_2$—$R_2$—$R_1$;
(b) $R_1$—$R_1$—$R_2$—$R_2$—$R_1$—$R_2$—$R_2$—$R_1$;
(c) $R_2$—$R_1$p13 $R_1$—$R_2$—$R_2$—R1—$R_2$—$R_2$—$R_1$;
(d) $R_2$—$R_2$—$R_1$—$R_1$—$R_2$—$R_2$—$R_1$—$R_2$—$R_2$—$R_1$; and
(e) $R_1$—$R_2$—$R_2$—$R_1$—$R_1$—$R_2$—$R_2$—$R_1$— $R_2$—$R_2$—$R_1$, wherein $R_1$ and $R_2$ are as hereinabove described.

In one embodiment, the peptide has the structure (a), and a representative example of such a structure is (SEQ ID NO: 13), which is given in the accompanying sequence listing.

In another embodiment, the peptide has the structure (b), and a representative example of such a structure is (SEQ ID NO:14), which is given in the accompanying sequence listing.

In another embodiment, the peptide has the structure (c), and a representative example of such a structure is (SEQ ID NO: 15) as given in the accompanying sequence listing.

In yet another embodiment, the peptide has the structure (d), and a representative example of such a structure is (SEQ ID NO:16) as given in the accompanying sequence listing.

In a further embodiment, the peptide has the structure (e), and representative examples of such a structure are (SEQ ID NO:17) and (SEQ ID NO:18) as given in the accompanying sequence listing.

In accordance with another aspect of the present invention, there is provided a biologically active amphiphilic peptide having the following structural formula:

(SEQ ID NO:19).

In general, the peptides hereinabove described are ion channel-forming peptides.

An ion channel-forming peptide or ionophore is a peptide which increases the permeability for ions across a natural or synthetic lipid membrane. B. Christensen et al., *PNAS*, Vol. 85 Pgs. 5072–76 (July, 1988) and Anzai, et al., *Biochimica et Biographysica Acta.*, Vol. 1064, pgs. 256–266 (1991), describe methodology which indicates whether or not a peptide has ion channel-forming properties and is therefore an ionophore. As used herein an ion channel-forming peptide is a peptide which has ion channel-forming properties as determined by the method of Christensen et al or Anzai, et al.

In one embodiment, the hereinabove described peptides may be acetylated with a $CH_3CO$-group aid the N-terminal, said $CH_3CO$-group being hereinafter referred to by the letter X.

In another embodiment, the hereinabove described peptides may include an octanoyl group at the N-terminal.

In accordance with one embodiment, each of the amino acid residues contained in the peptides which is not glycine, is a D-amino acid residue. Although the scope of this particular embodiment is not to be limited to any theoretical reasoning, it is believed that the above-mentioned peptides, when consisting entirely of D-amino acid or glycine residues, may have increased resistance to proteolytic enzymes while retaining their biological activity. Such peptides thus may be administered orally. Also, in accordance with another embodiment, all of the amino acid residues may be D-amino acid or glycine residues, or L-amino acid or glycine residues.

In general, the peptides and/or analogues or derivatives thereof are generally water soluble to a concentration of at least 20 mg/ml at neutral pH in water. In addition, the structure of such peptide provides for flexibility of the peptide molecule. When the peptide is placed in water, it does not assume an amphiphilic structure. When the peptide encounters an oily surface or membrane, the peptide chain folds upon itself into a rod-like structure.

The peptides and/or analogues or derivatives thereof may be administered to a host; for example a human or non-human animal, in an amount effective to inhibit growth of a target cell, virus, or virally-infected cell. Thus, for example, the peptides and/or analogues or derivatives thereof may be used as antimicrobial agents anti-viral agents, anti-bacterial agents, anti-tumor agents, anti-parasitic agents, spermicides, as well as exhibiting other bioactive functions.

The term "antimicrobial" as used herein means that the polypeptides of the present invention inhibit, prevent, or destroy the growth or proliferation of microbes such as bacteria, fungi, viruses, or the like.

The term "anti-bacterial" as used herein means that the polypeptides employed in the present invention produce effects adverse to the normal biological function of bacteria, including death or destruction and prevention of the growth or proliferation of the bacteria when contacted with the polypeptides.

The term "antibiotic" as used herein means that the peptides employed in the present invention produce effects adverse to the normal biological functions of the non-host cell, tissue or organism, including death or destruction and prevention of the growth or proliferation of the non-host cell, tissue, or organism when contacted with the peptides.

The term "spermicidal" as used herein means that the polypeptides employed in the present invention, inhibit, prevent, or destroy the motility of sperm.

The term "antiviral" as used herein means that the polypeptides employed in the present invention inhibit, prevent, or destroy the growth or proliferation of viruses, or of virally-infected cells.

The term "anti -tumor" as used herein means that the polypeptide inhibits the growth of or destroys tumors, including cancerous tumors.

The term "anti-parasitic" as used herein means that the polypeptides employed in the present invention inhibit, prevent, or destroy the growth or prolifiration of parasites.

The peptides of the present invention have a broad range of potent antibiotic activity against a plurality of microorganisms including gram-positive and gram-negative bacteria, fungi, protozoa, and the like, as well as parasites. The peptides of the present invention allow a method for treating or controlling microbial infection caused by organisms which are sensitive to the peptides. Such treatment may comprise administering to a host organism or tissue susceptible to or affiliated with a microbial infection an antimicrobial amount of at least one of the peptides.

Because of the antibiotic, antimicrobial, antiviral, and antibacterial properties of the peptides, they may also be used as preservatives or sterilants or disinfectants of materials susceptible to microbial or viral contamination.

The peptides and/or derivatives or analogues thereof may be administered in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule, or the like. The peptide compositions may also be used in combination with adjuvants, protease inhibitors, or compatible drugs where such a combination is seen to be desirable or advantageous in controlling infection caused by harmful microorganisms including protozoa, viruses, and the like, as well as by parasites.

The peptides of the present invention may be administered to a host; in particular a human or non-human animal, in an effective antibiotic and/or anti-tumor and/or anti-viral and/or anti-microbial and/or antibacterial and/or anti-parasitic and/or an antispermicidal amount.

Depending on the use, a composition in accordance with the invention will contain an effective anti-microbial amount and/or an effective antispermicidal amount and/or an effective anti-viral amount and/or an effective anti-tumor amount and/or an effective anti-parasitic and/or an effective antibiotic amount of one or more of the hereinabove described peptides which have such activity. The peptides may be administered by direct application of the peptides to the target cell or virus or virally-infected cell, or indirectly applied through systemic administration.

The peptides of the present invention may also be employed in promoting or stimulating healing of a wound in a host.

The term "wound healing" as used herein includes various aspects of the wound healing process.

These aspects include, but are limited to, increased contraction of the wound, increased deposition of connective tissue, as evidenced by, for example, increased deposition of collagen in the wound, and increased tensile strength of the wound, i.e., the peptides increase wound breaking strength. The peptides of the present invention may also be employed so as to reverse the inhibition of wound healing caused by conditions which depress or compromise the immune system.

The peptides of the present invention may be used in the treatment of external burns and to treat and/or prevent skin and burn infections. In particular, the peptides may be used to treat skin and burn infections caused by organisms such as, but not limited to, *P. aeruginose* and *S. aureus*.

The peptides are also useful in the prevention or treatment of eye infections. Such infections may be caused by bacteria such as, but not limited to, *P. aeruginosa, S. aureus*, and *N. gonorrhoeae*, by fungi such as but not limited to *C. albicans* and *A. fumigatus*, by parasites such as but not limited to *A. castellani*, or by viruses.

The peptides may also be effective in killing cysts, spores, or trophozoites of infection—causing organisms. Such organisms include, but are not limited to Acanthamoeba which forms trophozoites or cysts, *C. albicans*, which forms spores, and *A. fumigatus*, which forms spores as well.

The peptides may also be administered to plants in an effective antimicrobial or antiviral of antiparasitic amount to prevent or treat microbial or viral or parasitic contamination thereof.

The peptides, when used in topical compositions, are generally present in an amount of at least 0.1%, by weight. In most cases, it is not necessary to employ the peptide in an amount greater than 2.0%, by weight.

In employing such compositions systemically (intramuscular, intravenous, intraperitoneal), the active peptide is present in an amount to achieve a serum level of the peptide of at least about 5 ug/ml. In general, the serum level of peptide need not exceed 500 ug/ml. A preferred serum level is about 100 ug/ml. Such serum levels may be achieved by incorporating the peptide in a composition to be administered systemically at a dose of from 1 to about 10 mg/kg. In general, the peptide(s) need not be administered at a dose exceeding 100 mg/kg.

The peptides may be produced by known techniques and obtained in substantially pure form. For example, the peptides may be synthesized on an automatic peptide synthesizer. *Journal of the American Chemical Society,* Vol. 85, pgs. 2149–54 (1963). It is also possible to produce such peptides by genetic engineering techniques.

Thus, within the scope of the present invention there may be provided DNA which encodes the peptides hereinabove described. Such DNA may be expressed by means known to those skilled in the art. Thus, it is also contemplated that within the scope of the present invention the peptides may be administered by administering to a host DNA which encodes the peptide(s).

In accordance with another embodiment, the peptides of the present invention may be employed in combination with an ion having phamacological properties for the purposes hereinabove described.

An ion having pharmacological properties is one which when introduced into a target cell, virus, or virally-infected cell, inhibits and/or prevents and/or destroys the growth of the target cell, virus, or virally-infected cell.

Such an ion having pharmacological properties is one which in the absence of an ion channel forming peptide is unable to cross a natural or synthetic lipid membrane; in particular a cell membrane, in sufficient amounts to affect a cell or virus adversely.

The peptide and ion having pharmacological properties may be administered as a single composition or in separate compositions, and the single or separate compositions may include additional materials, actives and/or inactives, in addition to the peptide and ion having pharmacological properties. As representative examples of ions having pharmacological properties which may be employed, there may be mentioned fluoride, peroxide, bicarbonate, silver, zinc, mercury, arsenic, copper, platinum, antimony, gold, thallium, nickel, selenium, bismuth, and cadmium ions.

The peptide and the ion having pharmacological properties, whether administered or prepared in a single composition or in separate compositions, are employed in amounts effective to inhibit and/or prevent and/or destroy the growth of the target cell. In effect, the ion potentiates the action of the peptide, i.e., the amount of ion i s effective to reduce the maximum effective concentration of the peptide or protein for inhibiting growth of a target cell, virus, or vitally-infected cell.

The ion having pharmacological properties, when used topically, is generally employed in a concentration of from 0.05% to 2.0%. When used systemically, the ion is generally employed in an amount of from 1 to 10 mg. per kg. of host weight. Peptide dosages may be within the ranges hereinabove described.

It is also to be understood that the peptide; and ion having pharmacological properties, may be delivered or administered in different forms; for example, the toxic ion may be administered orally, while the peptide may be administered by IV or IP.

As representative examples of administering the peptide or protein and ion for topical or local administration, the peptide could be administered in an amount of up to about 1% weight to weight and the ion delivered in an amount of about 50 mM (about 0.1%). Alternatively, the ion, in the form of a salt such as sodium fluoride, could be administered orally in conjunction with systemic administration of the peptide. For example, the peptide may be administered IV or IP to achieve a serum dose of 100 micrograms per milliliter (10 milligrams per kilogram) in conjunction with an oral dose of ion, in particular, sodium fluoride, of 10 meq per kilogram.

In accordance with another embodiment, the peptides of the present invention may be administered to a host in combination with an antibiotic selected from the class consisting of bacitracins, gramacidin, polymyxin, vancomycin, teichoplanin, aminoglycosides, hydrophobic antibiotics, penicillins, monobactams, or derivatives or analogues thereof.

The bacitracins, gramacidin, polymyxin, vancomycin, teichoplanin, and derivatives and analogues thereof, are a group of polypeptide antibiotics. A preferred bacitracin is bacitracin A.

Aminoglycoside antibiotics include tobramycin, kanamycin, amikacin, the gentamicins (e.g., gentamicin $C_1$, gentamicin $C_2$, gentamicin $C_{1a}$), netilmicin, and derivatives and analogues thereof. The preferred aminoglycosides are tobramycin and the gentamicins. The aminoglycosides, and the bacitracins hereinabove described, tend to be hydrophilic and water-soluble.

Penicillins which may be employed include, but are not limited to benzyl penicillin, ampicillin, methicillin (dimethoxyphenyl penicillin), ticaricillin, penicillin V (phenoxymethyl penicillin), oxacillin, cloxacillin, dicloxacillin, flucloxacillin, amoxicillin, and amidinocillin. Preferred penicillins which may be employed are benzyl penicillin and ampicillin. A preferred monobactam which may be employed is aztreonam.

As representative examples of hydrophobic antibiotics which may be used in the present invention, there may be mentioned macrolides such as erythromycin, roxythromycin, clarithromycin, etc.; 9-N-alkyl derivatives of erythromycin; midecamycin acetate; azithromycin; flurithromycin; rifabutin; rokitamycin; a 6-O-methyl erythromycin A known as TE-031 (Taisho); rifapentine; benzypiperazinyl rifamycins such as CGP-7040, CGP-5909, CGP-279353 (Ciba-Geigy); an erythromycin A derivative with a cyclic carbamate fused to the $C_{11}/C_{12}$ position of a macrolide ring known as A-62514 (Abbott); AC-7230 (Toyo Jozo) benzoxazinorifamycin; difficidin; dirithromycin; a 3-N-piperdinomethylzaino methylrifamycin SV known as FCE-22250 (Farmitalia); M-119-a (Kirin Brewery); a 6-O-methyl-1-4"-O-carbamoyl erythromycin known as A-63075 (Abbott); 3-formylrifamycin SV-hydrazones with diazabicycloalkyl side chains such as CGP-27557 and CGP-2986 (Ciba-Geigy); and 16-membered macrolides having a 3-O-alpha-L-cladinosyl moiety, such as 3-O-alpha-L-cladinosyldeepoxy rosaramicin; tylosins and acyldemycinosyl tylosins.

In addition to the macrolides hereinabove described, rifamycin, carbenicillin, and nafcillin may be employed as well.

Other antibiotics which may be used (whether or not hydrophobic) are antibiotics which are 50-S ribosome inhibitors such as lincomycin; clindamycin; and chloramphenicol; etc.; antibiotics which have a large lipid like lactone ring, such as mystatin; pimaricin; etc.

The peptide and antibiotic may be adminstered by direct administration to a target cell or by systemic or topical administration to a host which includes the growth cell, in order to prevent, destroy or inhibit the growth of a target cell. Target cells whose growth may be prevented, inhibited, or destroyed by the administration of the peptides and antibiotic include Gram-positive and Gram-negative bacteria as well as fungal cells.

The antibiotic, such as those hereinabove described, derivatives or analogues thereof, when used topically, is generally employed in a concentration of about 0.1% to about 10%. When used systemically, the antibiotic or derivative or analogue thereof is generally employed in an amount of from 1.25 mg. to about 45 mg. per kg. of host weight per day. Peptide dosages may be those as hereinabove described.

As representative examples of administering the peptide and antibiotic for topical or local administration, the peptide could be administered in an amount of from about 0.1% to about 10% weight to weight, and the antibiotic is delivered in an amount of from about 0.1% to about 10% weight to weight.

In accordance with another embodiment, the peptides of the present invention may be administered in combination with an antiparasitic agent or an antifungal agent.

Antiparasitic agents which may be employed include, but are not limited to, anti-protozoan agents. Examples of specific anti-parasitic agents which may be employed include, but are not limited to, pentamidine isethionate, and propamidine isethionate (Brolene).

Anti-fungal agents which may be employed include, but are not limited to, ketoconazole. It is also to be understood that certain anti-parasitic agents, may also have anti-fungal activity, and that certain anti-fungal agents may have anti-parasitic activity.

In accordance with another embodiment, the peptides of the present invention may be administered in combination with an antibiotic which inhibits DNA gyrase, which is an enzyme involved in the formation of bonds between individual coiling strands of replicating bacterial DNA. Thus, DNA gyrase is necessary for the normal replication of bacterial DNA, and, therefore, antibiotics which inhibit DNA gyrase inhibit the normal replication of bacterial DNA.

Examples of antibiotics which inhibit DNA gyrase include nalidixic acid, oxolinic acid, cinoxacin, and quinolone antibiotics which include ciprofloxacin, norfloxacin, ofloxacin, enoxacin, pefloxacin, lomefloxacin, fleroxacin, tosulfloxacin, temafloxacin, and rufloxacin.

In accordance with another embodiment, the peptides of the present invention may be administered for the purpose hereinabove described in combination with other biologically active amphiphilic peptides, or in combination with ion channel-forming proteins.

The present invention will be further described with respect to the following example; however, the scope of the invention is not to be limited thereby.

EXAMPLE

Table I, which follows, indicates the Minimal Inhibitory Concentration (MIC) in µg/ml of Peptides (SEQ ID NO:1) through (SEQ ID NO:3), (SEQ ID NO:5), (SEQ ID NO:6), (SEQ ID NO:9) through (SEQ ID NO:11), and (SEQ ID NO:17) against S.aureus strain ATCC 25923, P. aeruginosa strain ATCC 27853, and E.coli ATCC strain 25922.

The procedure for the antibacterial assay is based upon the guidelines of the National Committee for Clinical Laboratory Standards, Document M7–T2, Volume 8, No. 8, 1988.

Stock solutions of peptides (SEQ ID NO: 1) through (SEQ ID NO:3), (SEQ ID NO:5), (SEQ ID NO:S), (SEQ ID NO:9) through (SEQ ID NO:12), and (SEQ ID NO:18) in accordance with the present invention are prepared at a concentration of 512 µg/ml in sterile deionized distilled water and stored at −70° C. Each peptide is a C-terminal amide and may or may not be acetylated at the N-Terminus. An acetyl group at the N-terminus is indicated by an X.

The stock peptide solution is diluted in serial dilutions (1:2) down the wells of a microtiter plate so that the final concentrations of peptides in the wells are 0.25, 0.50, i, 2,4, 8, 16, 32, 64, 128, and 256 µg/ml. $1-5 \times 10^5$ CFUs/ml of either S. aureus ATCC 25923, E. coli ATCC 25922, or P. aeruginosa ATCC 27853 were added to the wells in full strength Mueller Hinton broth (BBL 11443) from a mid-log culture. The inoculum is standardized spectrophotometrically at 600 nm and is verified by colony counts. The plates are incubated for 16–20 hours at 37° C., and the minimal inhibitory concentration (MIC) for each peptide is determined. Minimal inhibitory concentration is defined as the lowest concentration of peptide which produces a clear well in the microtiter plate. The minimal inhibitory concentration of each of (SEQ ID NO:1) through (SEQ ID NO:3), (SEQ ID NO:5), (SEQ ID NO:6), (SEQ ID NO:9) through (SEQ ID NO:11), and (SEQ ID NO:17) is given in Table I below.

TABLE I

| Peptide | Minimal Inhibitory Concentration (µg/ml) | | |
|---|---|---|---|
| | S. aureus | P. aeruginosa | E. coli |
| X-(SEQ ID NO: 1)-NH$_2$ | 16 | 4,8 | 4 |
| (SEQ ID NO.: 1)-NH$_2$ | 64,128 | 8,16 | 8,16 |
| X-(SEQ ID NO: 2)-NH$_2$ | 16 | 16 | 8,16 |
| (SEQ ID NO.:2)-NH$_2$ | 16 | 16 | 8,16 |
| X-(SEQ ID NO: 3)-NH$_2$ | 64 | 16 | 8,16 |
| (SEQ ID NO.:3)-NH$_2$ | 64 | 16 | 8,16,32 |
| X-(SEQ ID NO: 5)-NH$_2$ | 4 | 8 | 32 |
| X-(SEQ ID NO: 6)-NH$_2$ | 16 | 128 | 8 |
| X-(SEQ ID NO: 9)-NH$_2$ | 16 | 8 | 64 |
| X-(SEQ ID NO: 10)-NH$_2$ | 16,32 | 16 | 64 |
| (SEQ ID NO: 11) | >256 | 256 | >256 |
| (SEQ ID NO: 17)-NH$_2$ | >256 | 32,64 | 64,128 |
| X-(SEQ ID NO: 17)-NH$_2$ | 256 | 8,16 | 32,64 |

The peptides of the present invention, whether administered alone or in combination with agents such as ions having pharmalogical properties, antibiotics, or other biologically active peptides or proteins as hereinabove described, may be employed in a wide variety of pharmaceutical compositions in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule or the like. The peptide and/or agent as hereinabove described may also be used in combination with adjuvants, protease inhibitors, or compatible drugs where such a combination is seen to be desirable or advantageous in controlling infection caused by harmful microorganisms including protozoa, viruses, parasites, fungi, and the like.

The peptide may be administered to a host in particular an animal, in an effective antibiotic and/or anti-tumor and/or antiviral and/or antimicrobial and/or antispermicidal and/or. antifungal and/or antiparasitic amount, or in an amount effective to stimulate wound healing in a host. The peptides may be administered either alone or in combination with an ion having pharmacological properties, antibiotic, or ion channel forming peptide or protein as hereinabove described. When the peptide is administered in combination with a ion having pharmacological properties, the activity of the peptide is potentiated.

When the peptide is administered in combination with an agent as hereinabove described, it is possible to administer the peptide and agent in separate forms. For example, the agent may be administered systemically and the peptide may be administered topically.

When the peptide is administered topically, it may be administered in combination with a water-soluble vehicle, said water-soluble vehicle being in the form of an ointment, cream, lotion, paste or the like. Examples of water-soluble vehicles which may be employed include, but are not limited to, glycols, such as polyethylene glycol, hydroxycellulose, and KY Jelly. The water-soluble vehicle preferably free of art oily substance.

The peptide may also be employed in combination with a ion having pharmacological properties, as hereinabove described in the form of an oral composition for oral hygiene. Such a composition may be incorporated into a wide variety of compositions and materials used for oral hygiene purposes, which include, but are not limited to, toothpastes, mouthwashes, tooth gels, and tooth powders. Such composition may thus be used to treat or prevent periodontal disease, to prevent or reduce plaque, and/or to prevent or treat or reduce dental caries. The peptide and toxic ion may be used to inhibit, prevent, or destroy the growth of *Streptococcus mutans*, which is associated with dental caries and periodontal disease.

Numerous modifications and variations of the present invention are possible in light of the above teachings; therefore, within the scope of the appended claims the invention may be practiced otherwise than as particularly described.

What is claimed is:

1. A biologically active amphiphilic peptide, said peptide having the following basic structure $X_{14}$: $R_1-R_2-R_2-R_1-R_1-R_2-R_2-R_1-R_2-R_2-R_1-R_1-R_2-R_2-R_3$, wherein $R_1$ is a hydrophobic amino acid, $R_2$ is a basic hydrophilic or neutral hydrophilic amino acid, and $R_3$ is a neutral hydrophilic amino acid.

2. A biologically active amphiphilic peptide, said peptide including the following basic structure $X_{20}$: $R_-R_1-R_3-R_2-R_1-R_1-R_1-R_1-R_1-R_1-R_2-R_1-R_1-R_2-R_2-R_1-R_1-R_2-R_2-R_1-$, wherein $R_1$ is a hydrophobic amino acid, $R_2$ is a basic hydrophilic or neutral hydrophilic amino acid, and $R_3$ is a neutral hydrophilic amino acid.

3. A biologically active amphiphilic peptide having a structure selected from the group consisting of:

(a) $R_1-R_2-R_2-R_{-R2}-R_2-R_1$;

(b) $R_1-R_1-R_2-R_2-R_1-R_2-R_1-R_1$;

(c) $R_2-R_1-R_1-R_2-R_2-R_1-R_2-R_2-R_1$;

(d) $R_2-R_2-R_1-R_1-R_2-R_2-R_1-R_2-R_2-R_1$; and (e) $R_1-R_2-R_2-R_1-R_1-R_2-R_2-R_1-R_2-R_2-R_1$, wherein $R_1$ is a hydrophobic amino acid, and $R_2$ is a basic hydrophilic or neutral hydrophilic amino acid.

4. A biologically active amphiphilic peptide, said peptide having the following structure: $R_2-R_2-R_1-R_1-R_2-$ $R_2-R_1-R_2-R_2-R_1-R_1-R_2-R_1-R_1$, wherein $R_1$ is a hydrophobic amino acid, and $R_2$ is a basic hydrophilic or neutral hydrophilic amino acid.

5. A biologically active amphiphilic peptide, said peptide having the following structure:

$(Y_{12})_a-X_{12}-(Z_{12})_b$, wherein $X_{12}$ is: $R_2-R_1-R_2-R_2-R_1-R_1-R_2-R_2-R_1-R_2-R_2$;

$Y_{12}$ is:
(i) $R_2$;
(ii) $R_1-R_2$;
(iii) $R_1-R_1-R_2$;
(iv) $R_2-R_1-R_1-R_2$; or
(v) $R_2-R_2-R_1-R_1-R_2$;

$Z_{12}$ is:
(i) $R_1$;
(ii) $R_1-R_1$;
(iii) $R_1-R_1-R_2$;
(iv) $R_1-R_1-R_2-R_2$; or
(v) $R_1-R_1-R_2-R_2-R_1$, wherein $R_1$ is a hydrophobic amino acid, and $R_2$ is a basic hydrophilic amino acid, and a is 0 or 1 and b is 0 or 1.

6. A biologically active amphiphilic peptide, said peptide having the following structure:

$(Y_{16})a-X_{16}-(Z_{16})b$, wherein $X_{16}$ is: $R_1-R_2-R_1-R_1-R_2-R_2-R_1-R_1-R_2-R_2-R_4$, wherein $R_1$ is a hydrophobic amino acid, $R_2$ is a basic hydrophilic or neutral hydrophilic amino acid, and $R_4$ is a neutral hydrophilic amino acid or proline;

$Y_{16}$ is:
(i) $R_1$;
(ii) $R_1-R_1$;
(iii) $-R_2-R_1-R_1$;
(iv) $-R_1-R_2-R_1-R_1$;
(v) $-R_1-R_1-R_2-R_1-R_1$;
(vi) $-R_2-R_1-R_1-R_2-R_1-R_1$; or
(vii) $-R_2-R_2-R_1-R_1-R_2-R_1-R_1$; and $Z_{16}$ is:
(i) $R_2$;
(ii) $-R_2-R_2$;
(iii) $-R_2-R_2-R_1$;
(iv) $-R_2-R_2-R_1-R_1$;
(v) $-R_2-R_2-R_1-R_1-R_2$;
(vi) $-R_2-R_2-R_1-R_1-R_2-R_2$; or
(vii) $-R_2-R_2-R_1-R_1-R_2-R_2-R_1$, wherein a is 0 or 1 and b is 0 or 1.

7. A biologically active amphiphilic peptide, said peptide having the following structure:

$(Y_{18})_a-X_{18}-(Z_{18})_b$, wherein $X_{18}$ is: $R_1-R_1-R_2-R_2-R_1-R_2-R_2-R_1-R_1-R_2-R_2-R_1-R_3$, wherein $R_1$ is a hydrophobic amino acid, $R_2$ is a basic hydrophilic or neutral hydrophilic amino acid, and $R_3$ is a neutral hydrophilic amino acid;

$Y_{18}$ is:
(i) $-R_1$;
(ii) $-R_2-R_1$;
(iii) $-R_2-R_2-R_1$;
(iv) $-R_1-R_2-R_2-R_1$;
(v) $-R_1-R_1-R_2-R_2-R_1$;
(vi) $-R_2-R_1-R_1-R_2-R_2-R_1$; or
(vii) $-R_2-R_2-R_1-R_1-R_2-R_2-R_1$; and $Z_{18}$ is:
(i) $-R_1$;
(ii) $-R_1-R_5$;
(iii) $-R_1R_5-R_5$;
(iv) $-R_1'R_5-R_5-R_3$;
(v) $-R_1-R_5-R_5-R_3-R_1$;
(vi) $-R_1-R_5-R_5-R_3-R_1-R_3$;
(vii) $-R_1-R_5-R_5-R_3-R_1-R_3-R_3$;
(viii) $-R_1-R_5-R_5-R_3-R_1-R_3-R_3-R_5$; or
(ix) $-R_1-R_5-R_5-R_3-R_1-R_3-R_3-R_5-R_3$, wherein $R_5$ is proline, a is or 1, and b is 0 or 1.

8. A biologically active amphiphilic peptide, said peptide having the following structure:

$X_{20}-Z_{20}$, wherein $X_{20}$ is:
$R_1-R_1-R_3-R_2-R_1-R_1-R_1-R_1-R_1-R_2-R_1-R_1-R_2-R_2-R_1-R_1-R_2-R_2-R_1$, wherein $R_1$ is hydrophobic amino acid, $R_2$ is a basic hydrophilic or neutral hydrophilic amino acid, and $R_3$ is a neutral hydrophilic amino acid; and $Z_{20}$ is:
(i) $-R_2$;
(ii) $R_2-R_2$;
(iii) $-R_2-R_2-R_1$;
(iv) $-R_2-R_2-R_1-R_1$;
(v) $-R_2-R_2-R_1-R_1-R_2$;
(vi) $-R_2-R_2-R_1-R_1-R_2-R_2$; or
(vii) $-R_2-R_2-R_1-R_1-R_2-R_2-R_1$.

* * * * *

UNITED STATES PATENT AND TRADEMARK OFFICE
CERTIFICATE OF CORRECTION

PATENT NO. : 5,470,950

DATED : November 28, 1995

INVENTOR(S) : Maloy et al.

It is certified that error appears in the above-indentified patent and that said Letters Patent is hereby corrected as shown below:

Claim 1, column 21, line 57, change ";" to --:--; and column 21, line 58, change

"$R_1—R_2—R_2—R_1—R_2—R_2—R_1—R_1—R_2—R_2— R_3,$"

to -- "$R_1—R_2—R_2—R_1—R_2—R_2—R_1—R_1—R_2—R_2—R_3,$ --.

Claim 2, column 21, line 63, after "x20:" change "$R\_\_—R_1—R_3—$" to

-- $R_1—R_1—R_3—$ --;

column 21, line 64, change

"$R_2 —R_1—R_1—R_1—R_1—R_1—R_1—R_2—R_1— R_1—R_2—$"

to -- $R_2—R_1—R_1—R_1—R_1—R_1—R_1—R_2—R_1—R_1—R_2,$ --

Claim 3, column 22, line 58, change "(a)

$R_1—R_2—R_2—R_{,\_R2}—R_2—R_1—;$" to -- (a) $R_1—R_2—R_2—R_1—R_2—R_2—R_1;$ --;

and, column 22, line 63, change

"(e) $R_1—R_2—R_2—R_1—R_1—R_2—R_2 —R_1—R_2—R_2—R_1,$" to

-- (e) $R_1—R_2—R_2—R_1—R_1—R_2—R_2—R_1—R_2—R_2—R_1,$ --.

UNITED STATES PATENT AND TRADEMARK OFFICE
CERTIFICATE OF CORRECTION

PATENT NO. : 5,470,950

DATED : November 28, 1995

INVENTOR(S) : Maloy et al.

It is certified that error appears in the above-indentified patent and that said Letters Patent is hereby corrected as shown below:

Claim 7, column 24, line 5, change

"$R_2-R_1-R_2-R_2-R_1-R_1-R_2-R_2-R_1-R_3$" to

--$R_2-R_1-R_2-R_2-R_1-R_1-R_2-R_2-R_1-R_3$"to column 24, line 22, change "(iii) —$R_1R_5-R_5$;" to -- (iii) —$R_1-R_5-R_5$; -- column 24, line 23, change "(iv) —$R_1'R_5-R_5-R_3$;"

to -- (iv) —$R_1-R_5-R_5-R_3$; --

UNITED STATES PATENT AND TRADEMARK OFFICE
CERTIFICATE OF CORRECTION

PATENT NO. : 5,470,950

DATED : November 28, 1995

INVENTOR(S) : Maloy et al.

It is certified that error appears in the above-indentified patent and that said Letters Patent is hereby corrected as shown below:

column 24, line 28, change

"(viii) $R_1-R_5-R_5-R_3-R_1 1-R_3-R_3-R_5$; or" to

-- (viii) $R_1-R_5-R_5-R_3-R_1-R_3-R_3-R_5$; or --.

column 24, line 29, change

"(ix) $-R_1-R_5-R_5-R_3-R_1-R_3-R_3 \quad -R_5-R_3$," to

-- (ix) $-R_1-R_5-R_5-R_3-R_1-R_3-R_3-R_5-R_3$, --.

UNITED STATES PATENT AND TRADEMARK OFFICE
CERTIFICATE OF CORRECTION

PATENT NO. : 5,470,950
DATED : November 28, 1995
INVENTOR(S) : Maloy et al

It is certified that error appears in the above-indentified patent and that said Letters Patent is hereby corrected as shown below:

Claim 8, column 24, line 34, change

"$R_1-R_1-R_3-R_2-R_1-R_1-R_1-R_1 13 \quad R_1-R_1-$" to

-- $R_1-R_1-R_3-R_2-R_1-R_1-R_1-R_1-R_1-R_1-$ --; and column 24, line 35, change "$R_2-R_1 \quad R_1-R_2-R_2-R_1- \quad R_1-R_2-R_2-R_1,$" to

-- $R_2-R_1-R_1-R_2-R_2-R_1-R_1-R_2-R_2-R_1,$ --.

Signed and Sealed this

Twentieth Day of August, 1996

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide,
            and/or may be acetylated at
            N- terminus.

( x i ) SEQUENCE DESCRIPTION:SEQ ID NO:1:

Leu Lys Lys Leu Lys Lys Leu Leu Lys Leu
                5                           10

Leu ( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide,
            and/or may be acetylated at
            N- terminus.

( x i ) SEQUENCE DESCRIPTION:SEQ ID NO:2:

Leu Leu Lys Lys Leu Lys Lys Leu Leu Lys
                5                           10

Leu Leu ( 2 ) INFORMATION FOR SEQ ID NO:3:

( i ) SEQUENCE CHARACTERISTICS:
        ( A ) LENGTH: 13 amino acids
        ( B ) TYPE: amino acid (C) STRANDEDNESS:
(D) TOPOLOGY: linear (i i) MOLECULE TYPE: peptide (i x) FEATURE:
(D) OTHER INFORMATION: May be a C-terminal amide,
and/or may be acetylated at
N-terminus.

(x i) SEQUENCE DESCRIPTION:SEQ ID NO:3:

Lys Leu Leu Lys Lys Leu Lys Lys Leu Leu
                  5                        10
Lys Leu Leu (2) INFORMATION FOR SEQ ID NO:4:

(i) SEQUENCE CHARACTERISTICS:
(A) LENGTH: 14 amino acids
(B) TYPE: amino acid
(C) STRANDEDNESS:
(D) TOPOLOGY: linear (i i) MOLECULE TYPE: peptide (i x) FEATURE:
(D) OTHER INFORMATION: May be a C-terminal amide,
and/or may be acetylated at
N-terminus.

(x i) SEQUENCE DESCRIPTION:SEQ ID NO:4:

Lys Lys Leu Leu Lys Lys Leu Lys Lys Leu
                  5                        10
Leu Lys Leu Leu (2) INFORMATION FOR SEQ ID NO:5:

(i) SEQUENCE CHARACTERISTICS:
(A) LENGTH: 16 amino acids
(B) TYPE: amino acid
(C) STRANDEDNESS:
(D) TOPOLOGY: linear (i i) MOLECULE TYPE: peptide (i x) FEATURE:
(D) OTHER INFORMATION: May be a C-terminal
amide, and/or may be acetylated at
N-terminus.

(i x) SEQUENCE DESCRIPTION: SEQ ID NO:5:

Lys Lys Leu Leu Lys Lys Leu Lys Lys Leu Leu Lys Lys Leu Arg Arg
                  5                        10                       15

(2) INFORMATION FOR SEQ ID NO:6:

(i) SEQUENCE CHARACTERISTICS:
(A) LENGTH: 16 amino acids
(B) TYPE: amino acid
(C) STRANDEDNESS:
(D) TOPOLOGY: linear (i i) MOLECULE TYPE: peptide (i x) FEATURE:
(D) OTHER INFORMATION: May be a C-terminal amide,
and/or may be acetylated at
N-terminus.

(x i) SEQUENCE DESCRIPTION:SEQ ID NO:6:

```
Lys  Leu  Lys  Lys  Leu  Leu  Lys  Lys  Leu  Lys
                    5                         10

Lys  Leu  Leu  Lys  Leu  Leu
                    15
```

( 2 ) INFORMATION FOR SEQ ID NO:7:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide,
           and/or may be acetylated at
           N- terminus.

( x i ) SEQUENCE DESCRIPTION:SEQ ID NO:7:

```
Leu  Lys  Lys  Leu  Leu  Lys  Lys  Leu  Lys  Lys
                    5                         10

Leu  Leu  Lys  Lys  Asn
                    15
```

( 2 ) INFORMATION FOR SEQ ID NO:8:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide,
           and/or may be acetylated at
           N-terminus, Xaa is homoserine.

( x i ) SEQUENCE DESCRIPTION:SEQ ID NO:8:

```
Leu  Lys  Lys  Leu  Leu  Lys  Lys  Leu  Lys  Lys
                    5                         10

Leu  Leu  Lys  Lys  Xaa
                    15
```

( 2 ) INFORMATION FOR SEQ ID NO:9:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide,
           and/or may be acetylated at
           N- terminus.

( x i ) SEQUENCE DESCRIPTION:SEQ ID NO:9:

```
Leu  Lys  Leu  Leu  Lys  Lys  Leu  Leu  Lys  Lys
                    5                         10

Asn  Lys  Lys  Leu  Leu  Lys  Lys  Leu
                    15
```

( 2 ) INFORMATION FOR SEQ ID NO:10:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide,
            and/or may be acetylated at
            N- terminus.

( x i ) SEQUENCE DESCRIPTION:SEQ ID NO:10:

Leu Lys Leu Leu Lys Lys Leu Leu Lys Lys
                   5                                  10

Pro Lys Lys Leu Leu Lys Lys Leu
                  15

( 2 ) INFORMATION FOR SEQ ID NO:11:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide,
            and/or may be acetylated at
            N- terminus.

( x i ) SEQUENCE DESCRIPTION:SEQ ID NO:11:

Leu Leu Lys Lys Leu Lys Lys Leu Leu Lys
                   5                                  10

Lys Leu Gln Gly Pro Pro Gln Gly Gln Ser
                  15                         20

Pro Gln ( 2 ) INFORMATION FOR SEQ ID NO:12:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide,
            and/or may be acetylated at
            N- terminus.

( x i ) SEQUENCE DESCRIPTION:SEQ ID NO:12:

Leu Ala Ser Lys Ala Gly Ala Ile Ala Gly
                   5                                  10

Lys Ile Ala Lys Lys Leu Leu Lys Lys Leu
                  15                         20

( 2 ) INFORMATION FOR SEQ ID NO:13:

( i ) SEQUENCE CHARACTERISTICS:
        ( A ) LENGTH: 7 amino acids
        ( B ) TYPE: amino acid (C) STRANDEDNESS:
            (D) TOPOLOGY: linear (i i) MOLECULE TYPE: peptide (i x) FEATURE:
            (D) OTHER INFORMATION: May be a C- terminal amide,
                and/or may be acetylated at
                N- terminus.

(x i) SEQUENCE DESCRIPTION:SEQ ID NO:13:

Leu Lys Lys Leu Lys Lys Leu
                 5

(2) INFORMATION FOR SEQ ID NO:14:

(i) SEQUENCE CHARACTERISTICS:
            (A) LENGTH: 8 amino acids
            (B) TYPE: amino acid
            (C) STRANDEDNESS:
            (D) TOPOLOGY: linear (i i) MOLECULE TYPE: peptide (i x) FEATURE:
            (D) OTHER INFORMATION: May be a C- terminal amide,
                and/or may be acetylated at
                N- terminus.

(x i) SEQUENCE DESCRIPTION:SEQ ID NO:14:

Leu Leu Lys Lys Leu Lys Lys Leu
                 5

(2) INFORMATION FOR SEQ ID NO:15:

(i) SEQUENCE CHARACTERISTICS:
            (A) LENGTH: 9 amino acids
            (B) TYPE: amino acid
            (C) STRANDEDNESS:
            (D) TOPOLOGY: linear (i i) MOLECULE TYPE: peptide (i x) FEATURE:
            (D) OTHER INFORMATION: May be a C- terminal amide,
                and/or may be acetylated at
                N- terminus.

(x i) SEQUENCE DESCRIPTION:SEQ ID NO:15:

Lys Leu Leu Lys Lys Leu Lys Lys Leu
                 5

(2) INFORMATION FOR SEQ ID NO:16:

(i) SEQUENCE CHARACTERISTICS:
            (A) LENGTH: 10 amino acids
            (B) TYPE: amino acid
            (C) STRANDEDNESS:
            (D) TOPOLOGY: linear (i i) MOLECULE TYPE: peptide (i x) FEATURE:
            (D) OTHER INFORMATION: May be a C- terminal amide,
                and/or may be acetylated at
                N- terminus.

(x i) SEQUENCE DESCRIPTION:SEQ ID NO:16:

Lys Lys Leu Leu Lys Lys Leu Lys Lys Leu
                 5                   10

( 2 ) INFORMATION FOR SEQ ID NO:17:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide,
            and/or may be acetylated at
            N- terminus.

( x i ) SEQUENCE DESCRIPTION:SEQ ID NO:17:

Leu Lys Lys Leu Leu Lys Lys Leu Lys Lys Leu
            5                    10

( 2 ) INFORMATION FOR SEQ ID NO:18:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide,
            and/or may be acetylated at
            N- terminus.

( x i ) SEQUENCE DESCRIPTION:SEQ ID NO:18:

Ala Lys Lys Leu Leu Lys Lys Leu Lys Lys Leu
            5                    10

( 2 ) INFORMATION FOR SEQ ID NO:19:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide,
            and/or may be acetylated at
            N- terminus.

( x i ) SEQUENCE DESCRIPTION:SEQ ID NO:19:

Leu Lys Lys Leu Leu Lys Lys Leu Lys Lys Leu
            5                    10

Leu Lys Arg